United States Patent
Luo et al.

(10) Patent No.: US 11,311,236 B2
(45) Date of Patent: Apr. 26, 2022

(54) DEVICE FOR DETERMINING LOCATION OF BLOOD VESSEL AND METHOD THEREOF

(71) Applicants: BOE TECHNOLOGY GROUP CO., LTD., Beijing (CN); HEFEI BOE OPTOELECTRONICS TECHNOLOGY CO., LTD., Anhui (CN)

(72) Inventors: Qiangqiang Luo, Beijing (CN); Yingxi Tai, Beijing (CN); Haitao Wang, Beijing (CN); Zhenfang Li, Beijing (CN)

(73) Assignees: BOE TECHNOLOGY GROUP CO., LTD., Beijing (CN); HEFEI BOE OPTOELECTRONICS TECHNOLOGY CO., LTD., Anhui (CN)

( * ) Notice: Subject to any disclaimer, the term of this patent is extended or adjusted under 35 U.S.C. 154(b) by 678 days.

(21) Appl. No.: 16/203,879

(22) Filed: Nov. 29, 2018

(65) Prior Publication Data

US 2019/0261917 A1 Aug. 29, 2019
US 2020/0268310 A9 Aug. 27, 2020

(30) Foreign Application Priority Data

Feb. 27, 2018 (CN) .......................... 201810161524.7

(51) Int. Cl.
*A61B 5/00* (2006.01)
*A61B 5/02* (2006.01)
(Continued)

(52) U.S. Cl.
CPC .............. *A61B 5/489* (2013.01); *A61B 5/021* (2013.01); *A61B 5/02007* (2013.01);
(Continued)

(58) Field of Classification Search
CPC ..... A61B 5/489; A61B 5/15003; A61B 5/021; A61B 5/02007; A61B 5/150748;
(Continued)

(56) References Cited

U.S. PATENT DOCUMENTS 9,087,147 B1 * 7/2015 Fonte ..................... A61B 6/507
10,849,555 B1 * 12/2020 Sullivan ............. A61B 5/02225
(Continued)

FOREIGN PATENT DOCUMENTS

CN          1397251 A    2/2003
JP       2006192288 A    7/2006
(Continued)

OTHER PUBLICATIONS

China Second Office Action, Application No. 201810161524.7, dated Feb. 26, 2021, 21 pps.: with English translation.
(Continued)

*Primary Examiner* — May A Abouelela
(74) *Attorney, Agent, or Firm* — Armstrong Teasdale LLP (57) ABSTRACT

Embodiments of the present disclosure provide a device for determining a location of a blood vessel and a method thereof. The device includes a plurality of sensors, a processor, and an indicating device. The plurality of sensors may detect pressure values at a plurality of skin locations in contact with the plurality of sensors. The processor may determine the location of the blood vessel based on the pressure values. The pressure value at the skin location corresponding to the location of the blood vessel is greater than the pressure values at both sides of the skin location in a direction perpendicular to a direction of the blood vessel. The indicating device may indicate the location of the blood vessel.

18 Claims, 4 Drawing Sheets

(51) Int. Cl.
  *A61B 5/15* (2006.01)
  *A61M 5/42* (2006.01)
  *A61B 5/021* (2006.01)
  *A61M 5/46* (2006.01)
  *A61B 5/026* (2006.01)

(52) U.S. Cl.
  CPC .... *A61B 5/15003* (2013.01); *A61B 5/150748* (2013.01); *A61B 5/6824* (2013.01); *A61M 5/42* (2013.01); *A61M 5/46* (2013.01); *A61B 5/026* (2013.01); *A61B 5/6831* (2013.01); *A61B 2562/028* (2013.01); *A61B 2562/0247* (2013.01); *A61B 2562/046* (2013.01); *G06T 2207/30101* (2013.01)

(58) Field of Classification Search
  CPC ..... A61B 5/6824; A61B 5/026; A61B 5/6831; A61B 2562/0247; A61B 2562/028; A61B 5/02; G06T 2207/30101
  USPC .................................................. 600/476, 481
  See application file for complete search history.

(56) References Cited

U.S. PATENT DOCUMENTS

| | | | |
|---|---|---|---|
| 2004/0158158 A1 | 8/2004 | Jensen et al. | |
| 2009/0018453 A1* | 1/2009 | Banet ................. | A61B 5/14551 600/493 |
| 2009/0221894 A1 | 9/2009 | Myklebust et al. | |
| 2010/0069764 A1 | 3/2010 | Kang | |
| 2014/0200867 A1* | 7/2014 | Lavi ....................... | G16H 30/20 703/2 |
| 2014/0243744 A1* | 8/2014 | Wood ................... | A61B 5/0062 604/116 |
| 2015/0173673 A1* | 6/2015 | Toth ....................... | A61B 5/389 600/301 |
| 2015/0216425 A1* | 8/2015 | Gladshtein ........... | A61B 8/0891 600/431 |
| 2015/0339847 A1* | 11/2015 | Benishti ................ | A61M 5/007 382/131 |
| 2016/0029900 A1* | 2/2016 | LaPlante .............. | A61B 5/6828 600/335 |
| 2016/0157787 A1* | 6/2016 | Merritt ............... | A61B 5/02007 600/486 |
| 2016/0166157 A1* | 6/2016 | Naghavi ............ | A61B 5/02405 600/324 |
| 2016/0287094 A1* | 10/2016 | Joseph ............... | A61B 5/14551 |
| 2016/0302672 A1* | 10/2016 | Kuri ..................... | A61B 5/0215 |
| 2016/0310017 A1* | 10/2016 | Banet ..................... | A61B 5/725 |
| 2016/0338601 A1* | 11/2016 | Yang ..................... | A61B 5/0059 |
| 2017/0065184 A1* | 3/2017 | Barak .................. | A61B 5/0507 |
| 2017/0086686 A1* | 3/2017 | Narasimhan ....... | A61B 5/02444 |
| 2017/0095171 A1* | 4/2017 | Park .................... | A61B 5/349 |
| 2017/0156706 A1* | 6/2017 | Joseph ..................... | A61B 8/04 |
| 2017/0340209 A1* | 11/2017 | Klaassen .................. | A61B 5/11 |
| 2017/0354331 A1* | 12/2017 | Borkholder ............ | G09B 23/30 |
| 2018/0078155 A1* | 3/2018 | Baek ..................... | G16H 50/50 |
| 2018/0098820 A1* | 4/2018 | Park ..................... | A61B 5/1079 |
| 2018/0132781 A1* | 5/2018 | Weli-Numbere ........................... A61B 5/15003 | |
| 2018/0168465 A1* | 6/2018 | Yamada ............. | A61B 5/02108 |
| 2018/0184909 A1* | 7/2018 | Nakamura ........... | A61B 5/6824 |
| 2018/0206734 A1* | 7/2018 | Lin .................... | A61B 5/02007 |
| 2018/0206746 A1* | 7/2018 | Narasimhan ......... | A61B 5/6826 |
| 2018/0317772 A1* | 11/2018 | Triboulet ............. | A61B 5/1079 |
| 2018/0325448 A1* | 11/2018 | Hembrador ........... | A61B 5/026 |
| 2018/0344173 A1* | 12/2018 | Tu ...................... | A61B 5/02158 |
| 2019/0110701 A1* | 4/2019 | Valdastri ................ | A61B 5/022 |
| 2019/0159688 A1* | 5/2019 | De Groot .......... | A61B 5/02007 |
| 2019/0200884 A1* | 7/2019 | Kuenen ................ | A61B 5/0215 |
| 2019/0282107 A1* | 9/2019 | Gelissen ............ | A61B 5/02255 |
| 2019/0282169 A1* | 9/2019 | Chen ..................... | A61B 5/681 |
| 2019/0307339 A1* | 10/2019 | Aelen .................. | A61B 5/4887 |
| 2019/0328328 A1* | 10/2019 | Haick .................... | A61B 5/021 |
| 2019/0365256 A1* | 12/2019 | De Groot ........... | A61B 5/02125 |
| 2019/0380645 A1* | 12/2019 | Kopperschmidt ... | A61B 8/0891 |
| 2019/0387984 A1* | 12/2019 | Lin .................... | A61B 5/02116 |

FOREIGN PATENT DOCUMENTS

| | | |
|---|---|---|
| JP | 2008237533 A | 10/2008 |
| JP | 2013244286 A | 12/2013 |
| KR | 20150136650 A | 12/2015 |

OTHER PUBLICATIONS

China First Office Action, Application No. 201810161524.7, dated Jul. 2, 2020, 15 pps.: with English translation.
Changhyun Pang et al., "Highly Skin-Conformal Microhairy Sensor for Pulse Signal Amplification", Advanced Materials, 2014, 7 pps.

* cited by examiner

DEVICE FOR DETERMINING LOCATION OF BLOOD VESSEL AND METHOD THEREOF

CROSS REFERENCE TO RELATED APPLICATIONS

This patent application claims the benefit and priority of Chinese Patent Application No. 201810161524.7 filed on Feb. 27, 2018, the disclosure of which is incorporated by reference herein in its entirety as part of the present application.

BACKGROUND

The present disclosure relates to the field of medical technology, and in particular, to a device for determining a location of a blood vessel and a method thereof.

When a physical examination is performed, blood analysis is needed. Therefore, blood sampling is an important part of a physical examination. With improvements of living standards, a proportion of obese people in a total population is getting higher and higher, and it is difficult to accurately find the location of blood vessels due to accumulation of fat. In addition, because blood vessels of children and the elderly are thin and weak, it is difficult to accurately locate the blood vessels.

BRIEF DESCRIPTION

Embodiments of the present disclosure provide a device for determining a location of a blood vessel and a method thereof.

A first aspect of the present disclosure provides a device for determining a location of a blood vessel. The device includes a plurality of sensors configured to detect pressure values at a plurality of skin locations in contact with the plurality of sensors, a processor configured to determine the location of the blood vessel based on the pressure values, wherein the pressure value at the skin location corresponding to the location of the blood vessel is greater than the pressure values at both sides of the skin location in a direction perpendicular to a direction of blood vessel, and a indicating device configured to indicate the location of blood vessel.

In an embodiment of the present disclosure, the processor is further configured to determine an arc of a skin protrusion at the location of blood vessel based on the pressure value at the location of the blood vessel, and determine a radius of the arc as a depth of blood vessel.

In an embodiment of the present disclosure, the indicating device is further configured to indicate the depth of the blood vessel.

In an embodiment of the present disclosure, the processor is further configured to determine a blood inflow area and a blood outflow area according to the pressure value at the location of blood vessel, the pressure value at the blood inflow area being greater than the pressure value at the blood outflow area. The indicating device is further configured to indicate a blood flow direction from the blood inflow area to the blood outflow area.

In an embodiment of the present disclosure, the device further includes a strap. The strap has an opening to expose a blood collection area. The plurality of sensors are located around the opening.

In an embodiment of the present disclosure, the indicating device is a display apparatus.

In an embodiment of the present disclosure, the display apparatus includes a first display screen and a second display screen. The first display screen and the second display screen are oppositely located at opposite sides of the opening.

In an embodiment of the present disclosure, the first display screen and the second display screen are configured to display an image representing the blood vessel based on the location of the blood vessel.

In an embodiment of the present disclosure, the plurality of sensors are arranged on a first surface of the strap and the display apparatus is arranged on a second surface of the strap.

In an embodiment of the present disclosure, an orthographic projection of the display apparatus on the strap is within a range of orthographic projections of the plurality of sensors on the strap.

In an embodiment of the present disclosure, the indicating device is located at one side of the opening.

In an embodiment of the present disclosure, the processor is located on the strap.

A second aspect of the present disclosure provides a method for determining a location of a blood vessel. The method includes detecting pressure values at a plurality of skin locations, determining a location of a blood vessel according to the pressure values, wherein the pressure value at the skin location corresponding to the location of the blood vessel is greater than the pressure values at both sides of the skin location in a direction perpendicular to a direction of the blood vessel, and indicating the location of the blood vessel.

In an embodiment of the present disclosure, the method further includes determining an arc of a skin protrusion at the location of the blood vessel based on the pressure value at the location of blood vessel, and determining a radius of the arc as a depth of the blood vessel.

In an embodiment of the present disclosure, the method further includes indicating the depth of the blood vessel.

In an embodiment of the present disclosure, the method further includes determining a blood inflow area and a blood outflow area based on the pressure value at the location of the blood vessel. The pressure value at the blood inflow area is greater than the pressure value at the blood outflow area.

In an embodiment of the present disclosure, indicating the location of the blood vessel includes displaying an image representing the blood vessel based on the location of the blood vessel.

In an embodiment of the present disclosure, the method further includes determining that a blood collection location is on an extension line of the displayed image.

A third aspect of the present disclosure provides a storage medium. Computer instructions are stored in the storage medium. The method of the second aspect of the present disclosure is performed when the computer instructions are executed by the processor.

A fourth aspect of the present disclosure provides an apparatus. The apparatus includes one or more processors. The one or more processors are configured to execute computer instructions to perform the method of the second aspect of the present disclosure.

Further adaptive aspects and scope will become apparent from the description provided herein. It should be understood that various aspects of the present disclosure may be implemented alone or in combination with one or more other aspects. It should also be understood that the description and specific embodiments are intended to be illustrative and are not intended to limit the scope of the present disclosure.

BRIEF DESCRIPTION OF THE DRAWINGS

The drawings described herein are for purposes of illustration of the selected embodiments only, rather than of all the possible embodiments, and are not intended to limit the scope of the present disclosure, in which.

DETAILED DESCRIPTION

To make the technical solutions and advantages of the embodiments of the present disclosure clearer, the technical solutions of the embodiments of the present disclosure will be clearly and completely described below in conjunction with the drawings of the embodiments of the present disclosure. It is apparent that the described embodiments are only a part of the embodiments of the present disclosure, and not all of them. All other embodiments obtained by a person of ordinary skill in the art based on the described embodiments of the present disclosure without creative labor are within the scope of the present disclosure. The embodiments of the present disclosure will be described in details below with reference to the drawings in conjunction with the embodiments. It should be noted that features in the embodiments of the present disclosure may be combined with each other without conflict.

Figure 1:
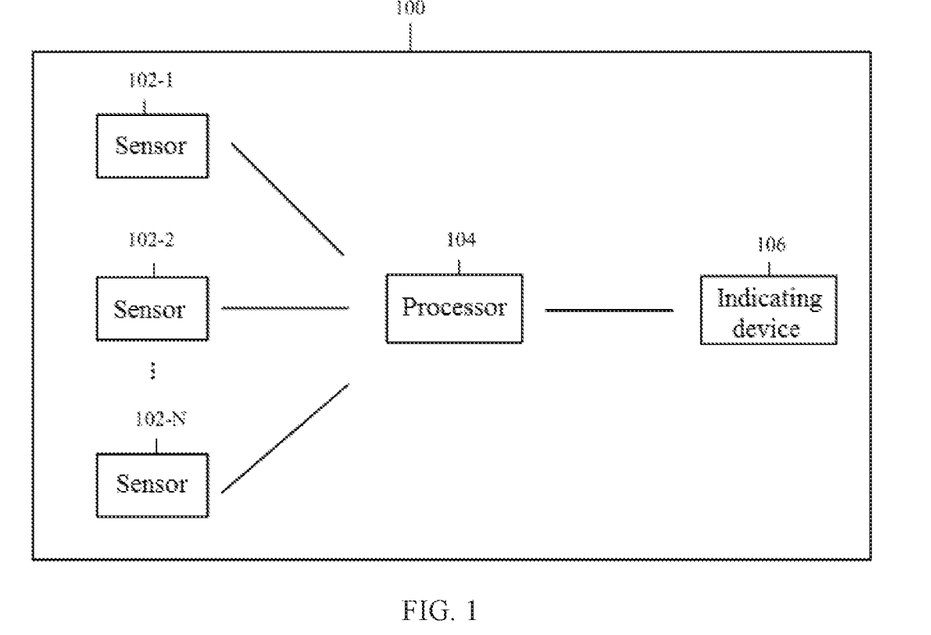
FIG. 1 shows a schematic block diagram of a device for determining a location of a blood vessel according to an embodiment of the present disclosure.

FIG. 1 shows a schematic block diagram of a device 100 for determining a location of a blood vessel according to an embodiment of the present disclosure. As shown in FIG. 1, the device 100 may include a plurality of sensors 102-1, 102-2, . . . , 102-N, a processor 104, and a indicating device 106. The sensors 102-1, 102-2, . . . , 102-N may be in contact with skin to detect pressure values at skin locations, respectively. The processor 104 may determine the location of the blood vessel based on the plurality of detected pressure values. In an embodiment, the pressure value at the skin location corresponding to the location of the blood vessel is greater than the pressure values at both sides of the skin location in a direction perpendicular to a direction of the blood vessel. The indicating device 106 may indicate the location of the blood vessel to the user (e.g., medical staff).

In an embodiment of the present disclosure, the sensors 102-1, 102-2, . . . , 102-N may be pressure sensors, such as Micro Electro Mechanical System (MEMS) pressure sensors. MEMS pressure sensors have a small size which may typically be a few microns. In this way, a pressure value may be accurately detected in a small skin area to improve the detection accuracy of the device 100.

In an embodiment of the present disclosure, the indicating device 106 may indicate the location of the blood vessel in various forms. In one embodiment, the indicating device may be a display that displays the location of the blood vessel by means of an image. In another embodiment, the indicating device may be a speaker that vocalizes the location of the blood vessel.

Figure 2A:
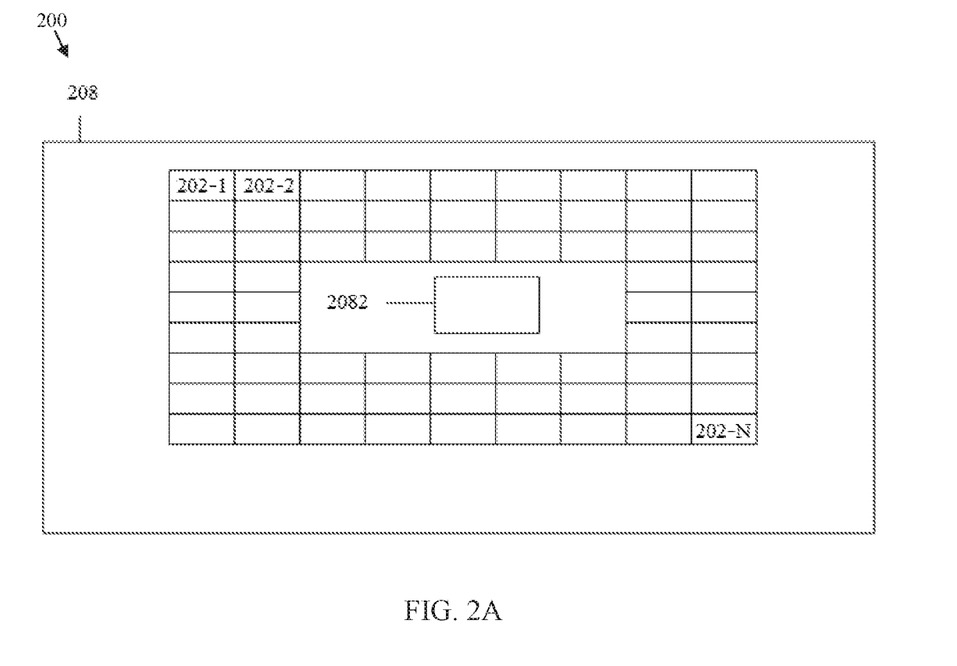
FIGS. 2A, 2B, and 2C show schematic diagrams of a device for determining a location of a blood vessel according to an embodiment of the present disclosure.
Figure 2B:
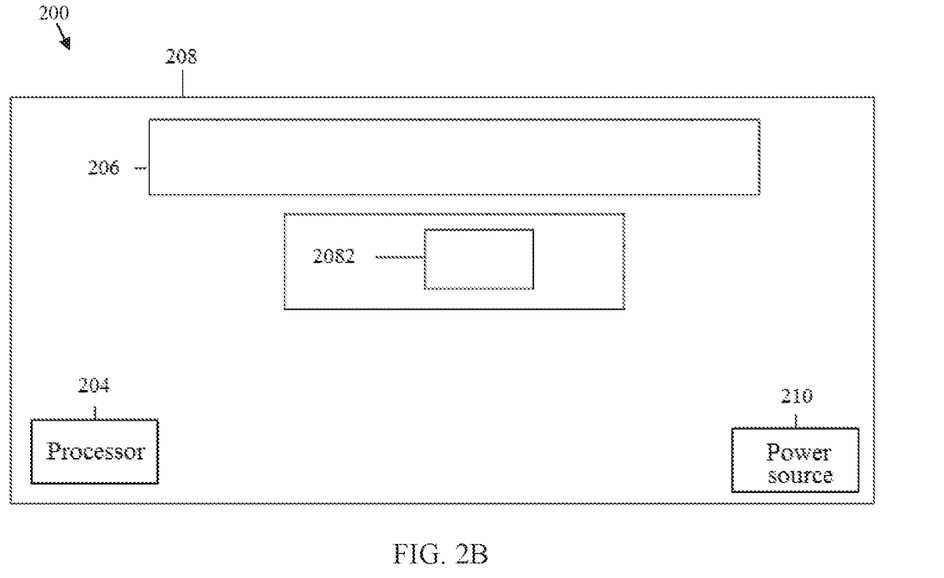
Figure 2C:
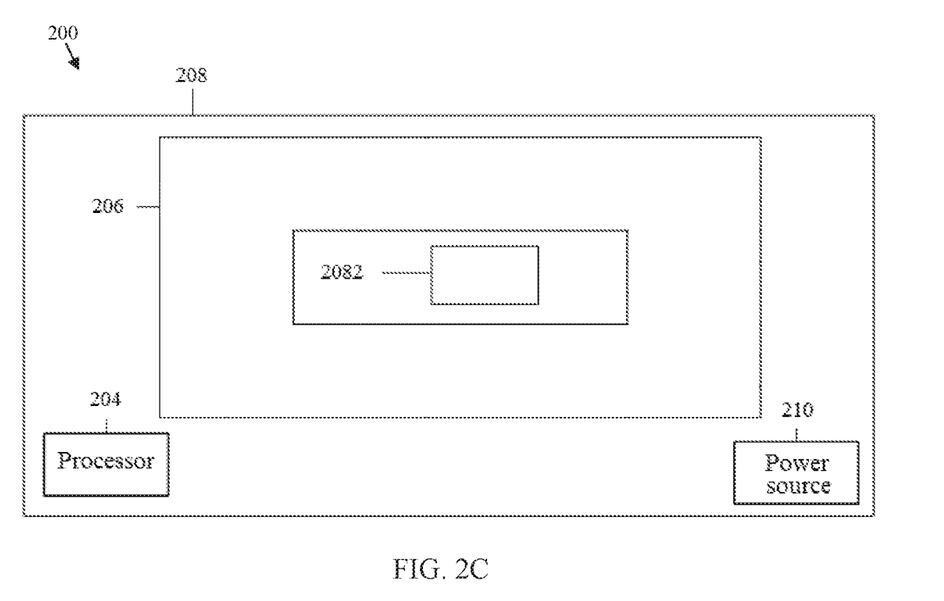

FIGS. 2A, 2B, and 2C show schematic diagrams of a device 200 for determining a location of a blood vessel according to an embodiment of the present disclosure. As shown in FIGS. 2A and 2B, the device 200 may also include a strap 208. The strap 208 may have an opening 2082 through which a blood collection area is exposed. The strap 208 has an inner surface (e.g., a first surface) and an outer surface (e.g., a second surface).

As shown in FIG. 2A, on the inner surface of the strap 208, sensors 202-1, 202-2, . . . , 202-N may be placed around the opening 2082. As shown in FIG. 2B, on the outer surface of the strap 208, an indicating device 206 may be placed on either side of the opening 2082. An orthographic projection of the indicating device 206 on the strap is within a range of orthographic projections of the plurality of sensors on the strap.

In another embodiment, as shown in FIG. 2C, on the outer surface of the strap, the orthographic projection of the indicating device 206 on the strap may also be the same as the orthographic projections of the plurality of sensors on the strap in FIG. 2A.

Further, in an embodiment of the present disclosure, as shown in FIGS. 2B and 2C, the processor 204 and a power source 210 may also be arranged on the strap 208 to improve the portability of the device 200. The power source 210 may be electrically connected to the plurality of sensors 202-1, 202-2, . . . , 202-N, the processor 204, and the indicating device 206, respectively, to provide power.

Alternatively, in other embodiments of the present disclosure, the processor 204 may be arranged external to the strap 208. In one embodiment, the processor 204 may be a local processor or a computing device. In this case, the processor 204 may be coupled to the sensors 202-1, 202-2, . . . , 202-N and the indicating device 206 via wires. In another embodiment, the processor 204 may be a remote processor or computing device in a cloud environment. In this case, the processor 204 may be coupled to the sensors 202-1, 202-2, . . . , 202-N and the indicating device 206 via a wired or wireless network.

When the device 200 as shown in FIGS. 2A, 2B, and 2C is employed, the strap 208 may be wrapped around a blood collection area of a human body, for example, the strap 208 may be wrapped around an arm to detect a location of a blood vessel on the arm. When the strap 208 is wrapped around blood collection area, pressure is exerted on the skin at that location. In this way, the inner surface of the strap 208 is brought into contact with the skin. Thus, the sensors 202-1, 202-2, . . . , 202-N arranged on the inner surface of the strap 208 may detect the pressure values at the plurality of skin locations in contact.

Those skilled in the art will appreciate that other means may also be employed to bring the sensors 202-1, 202-2, . . . , 202-N into contact with the skin to measure the pressure values at the skin locations in contact.

Figure 3:
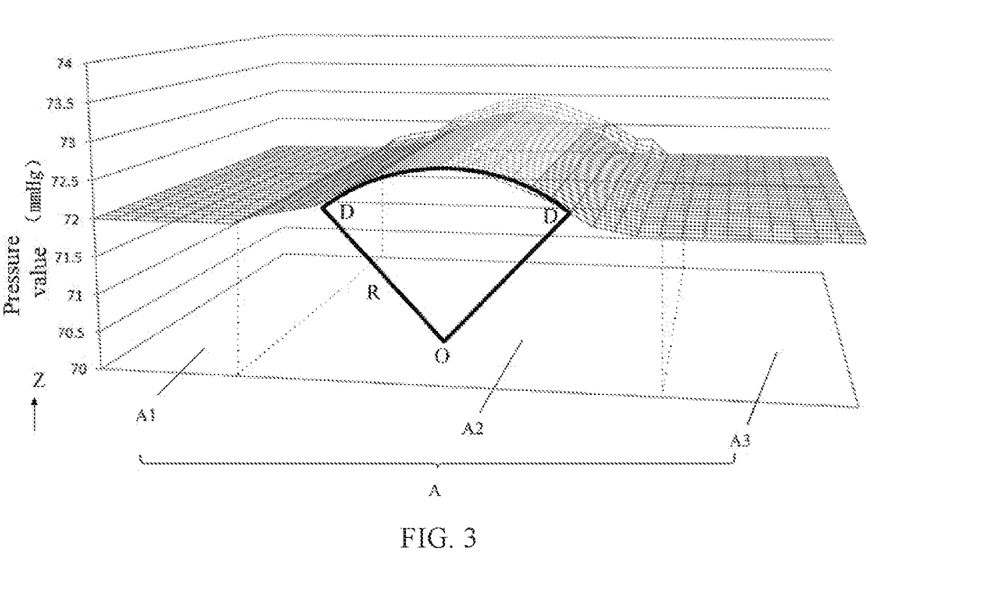
FIG. 3 shows an exemplary curve graph of pressure values detected by a plurality of sensors.

FIG. 3 shows an exemplary curve graph of pressure values detected by a plurality of sensors. In this example, as shown in FIG. 3, in a skin area A, a plurality of sensors are in contact with the skin. Each sensor may detect the pressure value at the location of the skin with which it is in contact. In FIG. 3, Z axis represents the pressure value. The processor may divide the area A into three subareas according to the plurality of pressure values detected by the sensors, namely, subarea A1, subarea A2, and subarea A3. In the subareas A1 and A3, the detected pressure values are substantially the same, and in the subarea A2, the detected pressure values are different from the pressure values detected in the adjacent subareas A1 and A3, for example, the pressure value detected at the subarea A2 is higher than the pressure value detected at the subareas A1 and A3. As shown, the detected pressure values in the subareas A1 and A3 are both 72 mmHg, and the detected pressure value in the subarea A2 is between 72 mmHg and 73 mmHg. Therefore, the processor may determine the location of the skin corresponding to the subarea A2 as the location of blood vessel.

Further, in an embodiment of the present disclosure, the processor may also determine the depth of the blood vessel based on the pressure value at the location of the blood vessel. In one embodiment, the processor may determine an arc of a skin protrusion at the location of the blood vessel based on the pressure value at the location of the blood vessel. The processor may then determine a radius of the arc as a depth of blood vessel.

In the above example, as shown in FIG. 3, the processor determines that the subarea A2 is the location of the blood vessel. In the subarea A2, the detected pressure value is between 72 mmHg and 73 mmHg, and gradually decreases towards both sides of the skin location in a direction perpendicular to a direction of the blood vessel. Therefore, the processor may determine a DD segment of the curve of the pressure value in the subarea A2 as the arc of the skin at the location of the blood vessel. Then, the processor may determine a corresponding center location O according to the arc, and determine a radius R of the arc according to an arc length formula $R=L*180/n\pi$, where L is an arc length corresponding to the arc, n is a central angle. Thus, the processor takes the determined radius R of the arc as a depth of the blood vessel. In this case, the indicating device may also indicate that the depth of blood vessel is R.

Figure 4:
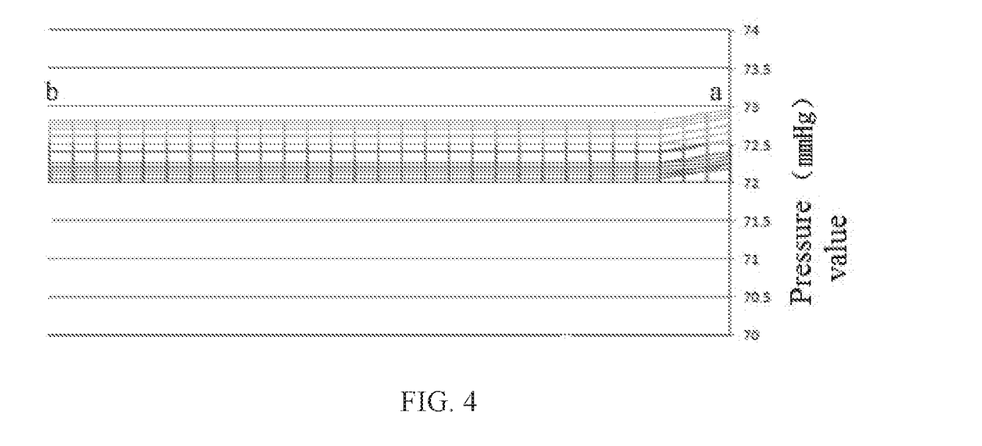
FIG. 4 shows an exemplary curve graph of pressure values at locations of blood vessels detected by a plurality of sensors.

Usually, when the strap is wrapped around the blood collection area of a human body, pressure is exerted to the blood vessel at that location, and the pressure value at the skin location where the blood flows in is different from that at the skin location where the blood flows out. Due to the inflow of blood, the pressure value at the location where the blood flows in is greater than that at the location where the blood flows out. FIG. 4 shows an exemplary curve graph of the pressure values at the locations of the blood vessels detected by a plurality of sensors. As shown in FIG. 4, among the plurality of pressure values at the locations of the blood vessels detected by the sensors, the pressure value at point a is greater than the pressure value at point b, so that the processor may determine that the location where the pressure value is higher is a blood inflow area, and the location where the pressure value is lower is a blood outflow area, that is, a blood flow direction is from a to b. By determining the blood flow direction, the processor may further determine a type of the blood vessel, such as an arterial or venous blood vessel, to assist the medical staff in collecting blood more efficiently. In an embodiment, the indicating device may also indicate the determined blood flow direction.

Figure 5:
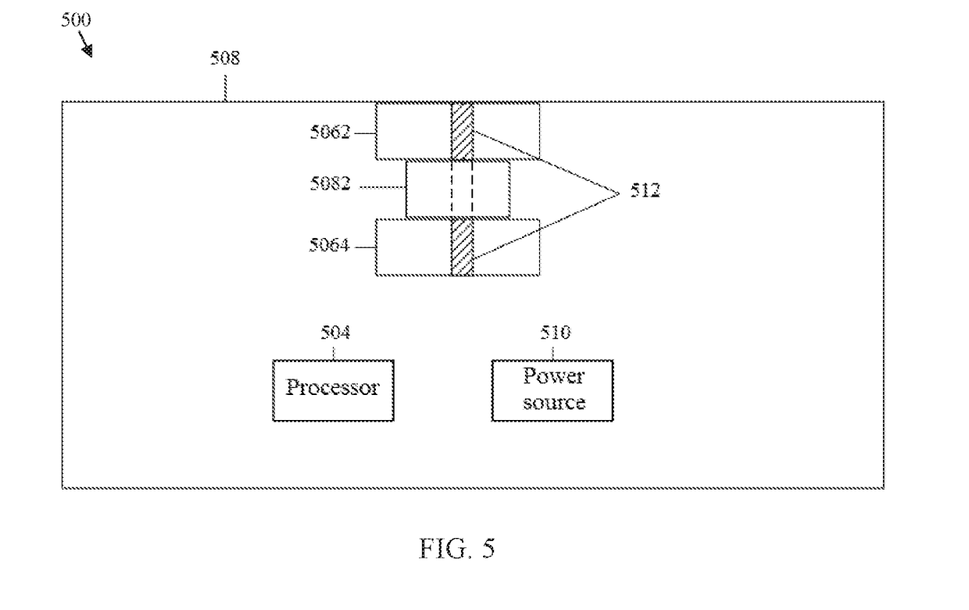
FIG. 5 shows a schematic diagram of a device for determining a location of a blood vessel according to an embodiment of the present disclosure.

FIG. 5 shows a schematic diagram of a device 500 for determining a location of a blood vessel according to an embodiment of the present disclosure. In the present embodiment, the indicating device in the device 500 is a display apparatus. As shown in FIG. 5, the display apparatus may include a first display screen 5062 and a second display screen 5064. As shown in FIG. 5, the first display screen 5062 and the second display screen 5064 are oppositely located at opposite sides of the opening 5082. The first display screen 5062 and the second display screen 5064 may visually display an image 512 representing the blood vessel based on the location of the blood vessel. Accordingly, the location of the blood vessel in the opening 5082 may be on an extension line of the displayed image 512, as shown by the dashed line in FIG. 5. Through the display, the location and the depth of the blood vessel may be displayed, so that the location and the depth of the blood vessel may be more intuitively indicated to the user.

In an embodiment of the present disclosure, the plurality of sensors may be located on a first surface of the strap and the display apparatus may be located on a second surface of the strap. For example, when a user wears a strap, a plurality of sensors located on the inner apparatus of the strap are in contact with the skin to detect the pressure values at a plurality of skin locations, and furthermore the user may see the location and the depth of the blood vessel through the display apparatus located on the outer surface of the strap. FIG. 5 illustratively shows only the outer surface of the strap.

Furthermore, the orthographic projection of the display apparatus on the strap may be located within the range of the orthographic projections of the plurality of sensors on the strap. In an embodiment of the present disclosure, the orthographic projections of the plurality of sensors on the strap may be the same as the orthographic projection of the display apparatus on the strap.

As may be seen from the above description, the device 500 according to an embodiment of the present disclosure can determine the location of the blood vessel so as to assist the user (e.g., medical staff) in accurately finding the location of the blood vessel to collect blood. In addition, the device 500 may also determine the depth of the blood vessel to avoid too deep or too shallow needle penetration during blood collection.

It will be appreciated that the device 500 may also be used in conjunction with an optical sensor. In this case, the location of the blood vessel may be determined by the optical sensor, and the depth of the blood vessel is determined by the device 500. In addition, the location of the blood vessel may also be determined by the optical sensor and the device 500, respectively, which is advantageous for the user to more accurately determine the location of the blood vessel.

Figure 6:
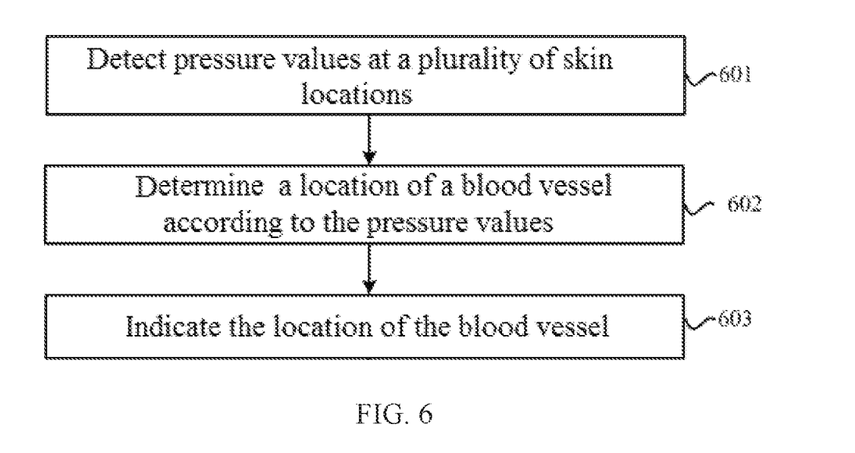
FIG. 6 shows a flow chart of a method for determining a location of a blood vessel according to an embodiment of the present disclosure.

FIG. 6 shows a flow chart of a method for determining a location of a blood vessel according to an embodiment of the present disclosure.

As shown in FIG. 6, in step S601, pressure values at a plurality of skin locations are detected.

In step S602, a location of a blood vessel is determined based on the detected pressure values. In a direction perpendicular to a direction of the blood vessel, the pressure value at the skin location corresponding to the location of the blood vessel is greater than the pressure values at both sides of the skin location. The process regarding the determination of the location of the blood vessel has been explained with reference to FIG. 3, and the description will not be repeated here.

In step S603, the location of the blood vessel is indicated. The location of the blood vessel can be indicated in many ways. In one embodiment, visual information (e.g., text, images) may be taken to indicate the location of the blood vessel. Alternatively, audible information (such as voice) may be taken to indicate the location of the blood vessel.

Further, in an embodiment of the present disclosure, a depth of the blood vessel may also be determined based on the detected pressure values. An arc of a skin protrusion at the location of the blood vessel is determined based on the pressure value at the location of the blood vessel, and then a radius of the arc is determined as the depth of the blood vessel. Moreover, the depth of the blood vessel is indicated. The process regarding the determination of the depth of the blood vessel has been explained with reference to FIG. 3, and the description will not be repeated here.

Further, in an embodiment of the present disclosure, the blood flow direction in the blood vessel may also be determined and indicated. Based on the pressure value at the location of the blood vessel, a blood inflow area and a blood outflow area are determined. The pressure value at the blood inflow area is greater than the pressure value at the blood outflow area.

Further, in an embodiment of the present disclosure, an image representing a blood vessel may be displayed according to the location of the blood vessel, for example, by a display apparatus. Alternatively, it may be determined that the blood collection location is on an extension line of the displayed image. In this way, the blood collection location may be presented to the user more intuitively.

As may be seen from the above description, the location of the blood vessel may be determined using the method according to an embodiment of the present disclosure, so as to assist the user (for example, medical staff) in accurately finding the location of the blood vessel to collect blood. In addition, the depth of the blood vessel may be determined to avoid too deep or too shallow needle penetration during blood collection, thereby further improving work efficiency.

The flowchart shown in FIG. 6 is for illustration only, and those skilled in the art may understand that various modifications may be made to the flowchart shown or the steps described therein.

In other embodiments of the present disclosure, a storage medium is further provided. Computer instructions are stored in the storage medium, wherein the computer instructions when run by the processor execute the steps of the method for determining the location of the blood vessel as shown in FIG. 6.

In other embodiments of the present disclosure, an apparatus is further provided. The apparatus may include one or more processors, wherein the one or more processors are configured to execute computer instructions to perform the steps of the method for determining the location of the blood vessel as shown in FIG. 6.

The above description is only concerning some embodiments of the present disclosure, and is not intended to limit the present disclosure. Various changes and modifications may be made by those skilled in the art to the present disclosure. Any modification, equivalent substitution and improvement, etc. made within the spirit and principle of the present disclosure are intended to be included within the scope of the present disclosure.

What is claimed is:

1. A device for determining a location of a blood vessel, the device comprising:
a plurality of sensors configured to detect pressure values at a plurality of skin locations in contact with the plurality of sensors;
a processor configured to:
determine the location of the blood vessel based on the pressure values, wherein a pressure value at a skin location corresponding to the location of the blood vessel is greater than the pressure values at both sides of the skin location in a direction perpendicular to a direction of the blood vessel;
determine an arc of a skin protrusion at the location of the blood vessel based on the pressure value at the location of the blood vessel; and
determine a radius of the arc as a depth of the blood vessel; and
an indicating device configured to indicate the location of the blood vessel.

2. The device according to claim 1, wherein the indicating device is further configured to indicate the depth of the blood vessel.

3. The device according to claim 1, wherein the processor is further configured to determine a blood inflow area and a blood outflow area according to the pressure value at the location of the blood vessel, wherein the pressure value at the blood inflow area is greater than the pressure value at the blood outflow area, and wherein the indicating device is further configured to indicate a blood flow direction from the blood inflow area to the blood outflow area.

4. The device according to claim 1, further comprising a strap, wherein the strap has an opening to expose a blood collection area, and wherein the plurality of sensors are located around the opening.

5. The device according to claim 4, wherein the indicating device is a display apparatus.

6. The device according to claim 5, wherein the display apparatus comprises a first display screen and a second display screen, the first display screen and the second display screen being oppositely located at opposite sides of the opening.

7. The device according to claim 6, wherein the first display screen and the second display screen are configured to display an image representing the blood vessel based on the location of the blood vessel.

8. The device according to claim 5, wherein the plurality of sensors are located on a first surface of the strap, and wherein the display apparatus is arranged on a second surface of the strap.

9. The device according to claim 8, wherein an orthographic projection of the display apparatus on the strap is within a range of orthographic projections of the plurality of sensors on the strap.

10. The device according to claim 4, wherein the indicating device is located at one side of the opening.

11. The device according to claim 4, wherein the processor is located on the strap.

12. A method for determining a location of a blood vessel, the method comprising:
detecting pressure values at a plurality of skin locations;
determining a location of a blood vessel according to the pressure values, wherein a pressure value at a skin location corresponding to the location of the blood vessel is greater than the pressure values at both sides of the skin location in a direction perpendicular to a direction of the blood vessel;
determining an arc of a skin protrusion at the location of the blood vessel based on the pressure value at the location of the blood vessel;
determining a radius of the arc as a depth of the blood vessel; and
indicating the location of the blood vessel.

13. The method according to claim 3, further comprising indicating the depth of the blood vessel.

14. The method according to claim 12, further comprising determining a blood inflow area and a blood outflow area based on the pressure value at the location of the blood vessel, the pressure value at the blood inflow area being greater than the pressure value at the blood outflow area.

15. The method according to claim 12, wherein indicating the location of the blood vessel comprises displaying an image representing the blood vessel based on the location of the blood vessel.

16. The method according to claim 15, further comprising determining that a blood collection location is on an extension line of the displayed image.

17. A storage medium, having stored thereon computer instructions, wherein the computer instructions when run by a processor execute the method according to claim 12.

18. An apparatus comprising one or more processors configured to execute computer instructions to perform the method according to claim 12.

* * * * *

UNITED STATES PATENT AND TRADEMARK OFFICE
CERTIFICATE OF CORRECTION

PATENT NO. : 11,311,236 B2
APPLICATION NO. : 16/203879
DATED : April 26, 2022
INVENTOR(S) : Qiangqiang Luo et al.

It is certified that error appears in the above-identified patent and that said Letters Patent is hereby corrected as shown below:

In the Claims

In Claim 13, Column 8, Line 61, delete "claim 3" and insert therefor -- claim 12 --.

Signed and Sealed this
Twenty-third Day of August, 2022

Katherine Kelly Vidal
*Director of the United States Patent and Trademark Office*